(12) United States Patent
de Graaff et al.

(10) Patent No.: US 8,291,910 B2
(45) Date of Patent: Oct. 23, 2012

(54) INTRAUTERINE DEPOSIT

(75) Inventors: Wouter de Graaff, Oss (NL); Harm Veenstra, Oss (NL); Titia Martine Truce Mulders, Oss (NL)

(73) Assignee: MSD Oss B.V., Oss (NL)

( * ) Notice: Subject to any disclaimer, the term of this patent is extended or adjusted under 35 U.S.C. 154(b) by 113 days.

(21) Appl. No.: 12/740,837

(22) PCT Filed: Nov. 7, 2008

(86) PCT No.: PCT/EP2008/065149
§ 371 (c)(1),
(2), (4) Date: Sep. 7, 2010

(87) PCT Pub. No.: WO2009/060077
PCT Pub. Date: May 14, 2009

(65) Prior Publication Data
US 2011/0017219 A1  Jan. 27, 2011

(30) Foreign Application Priority Data
Nov. 7, 2007  (EP) ..................................... 07120191

(51) Int. Cl.
*A61F 6/06* (2006.01)
*A61K 9/22* (2006.01)
(52) U.S. Cl. ...................... 128/833; 424/430; 604/891.1
(58) Field of Classification Search .................. 128/830, 128/831–833; 424/430, 422, 432, 433, 438; 604/890.1, 891.1, 892.1; 607/119, 126, 116, 607/122, 128; 600/375
See application file for complete search history.

(56) References Cited

U.S. PATENT DOCUMENTS

| | | | |
|---|---|---|---|
| 3,656,483 A * | 4/1972 | Rudel | 604/285 |
| 3,952,734 A | 4/1976 | Van Os et al. | |
| 4,102,998 A * | 7/1978 | Gutnick | 424/115 |
| 4,188,951 A * | 2/1980 | Higuchi et al. | 424/432 |
| 4,341,728 A | 7/1982 | Robertson et al. | |
| 7,080,647 B2 | 7/2006 | Wildemeersch | |

FOREIGN PATENT DOCUMENTS

| | | |
|---|---|---|
| DE | 2 101 533 | 1/1971 |
| DE | 41 25 575 C2 | 4/1995 |
| EP | 1 400 258 A1 | 3/2004 |
| WO | 96/01092 A1 | 1/1996 |
| WO | 2006/079709 A2 | 8/2006 |
| WO | 2006/079709 A3 | 8/2006 |

\* cited by examiner

*Primary Examiner* — Patricia Bianco
*Assistant Examiner* — Tarla Patel
(74) *Attorney, Agent, or Firm* — Janet E. Fair; John C. Todaro

(57) ABSTRACT

An intrauterine system (1) for the retention of a biologically active compound within the uterus of a female mammal is formed by a frame (16) defining an interior space (20) for receipt of a deposit of the compound (22). The frame has an open structure (18) allowing access to a substantial part of an outer surface of the deposit and the deposit has a rate controlling structure that controls a rate of release of the compound within the Uterus. Retention elements (6) are provided on the frame for retaining the frame within the uterus.

25 Claims, 4 Drawing Sheets

INTRAUTERINE DEPOSIT

CROSS REFERENCE TO RELATED APPLICATION

This application is entered into national stage examination under 37 U.S.C. 371 and stems from international patent application No. PCT/EP2008/065149 filed on Nov. 7, 2008.

BACKGROUND OF THE INVENTION

1. Field of the Invention

The invention relates generally to intrauterine systems and in particular to devices that are capable of retaining and releasing a biologically active compound within the uterus. The invention further relates to a method of manufacturing an intrauterine system having a biologically active compound deposited therein.

2. Description of the Related Art

The use of intrauterine devices (IUDs) has long been recognised as a convenient manner of providing long-term contraception. The presence of a device within the uterus causes the release of leukocytes and prostaglandins by the endometrium or uterine lining. These substances are hostile to both sperm and eggs and are understood to prevent fertilization and any subsequent attachment of the fertilized egg to the endometrium. The use of copper in an IUD increases the spermicidal effect.

An IUD that has been widely accepted is presently marketed by N.V. Organon under the name Multiload™. Such a device is depicted in U.S. Pat. No. 3,952,734 and comprises an elongated stem carrying at one end two resilient, cantilevered arms, extending sideways on either side of the stem. A copper wire is wound about the stem. For insertion into the uterine cavity the stem is contained within a tube shaped sheath by means of which the device may be inserted through the cervix. The sheath narrowly encloses the stem and the shape and flexibility of the arms are chosen such that they can collapse around the sheath during insertion. The sheath may then be pulled back and the arms unfold to retain the IUD within the uterus. For the purpose of retrieval, a thread is attached to the stem at the opposite end from the arms. The thread extends through the cervix and can be pulled for removal of the device. Under normal circumstances the IUD may be effectively used for long periods of up to 5 years without removal.

More recently, devices have been developed that can include a quantity of a hormone for long term retention and release within the uterus. These devices are generally referred to as intrauterine systems (IUS) and the term will be used hereafter to refer to IUDs having an incorporated agent. One system is marketed by Schering AG under the name Mirena™. The system comprises a T-shaped polyethylene frame with a steroid reservoir around the stem. The reservoir consists of a cylinder made of a mixture of levonogestrel and silicone. The reservoir is covered by a silicone membrane which controls the release rate to about 20 micrograms per day for a period of 3 to 5 years. Insertion and removal of the system is generally similar to that described above. Such a system is shown in U.S. Pat. No. 4,341,728. The use of steroids may enhance the contraceptive effect and also contribute to non-contraceptive health benefits of the system. Copper coil type IUDs tend to increase bleeding during a woman's menstrual cycle. Using a hormone based IUS, menstrual bleeding may be reduced or even stop. Local administration of hormones also allows lower dosages to be used compared to other hormonal methods for contraception whose primary mode of action is suppression of ovarian function. Another device that uses a dose of a progestogen to augment the effect of a copper coil is shown in German patent DE 4125575 C. According to the document, the progestogen may be provided in crystalline form in the head of the IUD and its release rate controlled by diffusion through fine pores or a perforation. Alternatively, it may be mixed in a silicone-gelatine material or a rubber based material and applied externally to the IUD.

To effectively control the pharmacodynamic properties, a system must be able to store a sufficient dose of agent to ensure a sufficient flux over a prolonged period, yet small enough to prevent injury or pain on passing through the cervix. Another difficulty encountered in manufacturing an IUS is the need to produce a structure that is strong enough to endure the forces of insertion, removal and usage without breaking yet again is small enough to prevent injury or pain on passing through the cervix. In particular, the connection between the arms and the stem must be flexible to allow folding of the arms around or within the inserter. On removal the arms must again fold without breaking off, since loss of part of the device within the uterus could lead to complications. One device that attempts to solve these problems is shown in U.S. Pat. No. 7,080,647, in which arms are attached to a slot in a medicated fibre stem. The strength of the device appears to be dependent upon the limited material available for the slot connection. Another device is known from WO96/01092 in which a medicated deposit is used to form the arms of the device and the stem comprises a loop that encircles the arms.

A further difficulty lies in ensuring correct dosage of the agent. Prior devices use rate controlling membranes surrounding the agent. The need for integrity of the membrane has required complicated moulding procedures for connecting the body of the device to the agent deposit. EP1400258 and WO06/079709 describe solutions for manufacture of IUSs. A number of other IUSs are disclosed in which a quantity of agent is provided e.g. as a coating at an external surface of the device Another alternative device is known from U.S. Pat. No. 3,656,483 which discloses a tubular body having perforations that allow for the release of a biologically active material. The material is in the form of a series of pellets that are biased towards the perforations by a spring member. Leaching of the medication takes place at the perforated region and the rate of release is controlled by the passage of the agent through the perforations. As each pellet is dissolved, the remaining pellets are pushed downwards by the spring. In this manner a series of different agents may be released successively. Nevertheless, the release rate of each agent is dependent upon the interrelation between the formulation and the perforations in the tubular body. Any blockages of the perforations would affect the subsequent release of the medication. The strength of the structure is provided by the external tube, which may make device insertion more difficult and painful.

It would be desirable to be able to manufacture a simple device in which the release rate of the medication or agent could be easily predicted. The rate should also be reliably maintained in practice. Furthermore, the construction of the device should be simple and involve a minimum number of components and yet be both strong and flexible and small enough to allow easy insertion.

BRIEF SUMMARY OF THE INVENTION

The present invention addresses these problems by providing an intrauterine system for the retention of a biologically active compound within the uterus of a female mammal, preferably a human. The system comprises a deposit of the compound, the deposit comprising a rate controlling structure that controls a rate of release of the compound within the uterus, a frame defining an interior space for receipt of the deposit, the frame having an open structure allowing access to a substantial part of an outer surface of the deposit and having one or more retention elements for retaining the frame within the uterus. Because of the open structure of the frame the greater part of the surface of the inserted deposit is directly exposed to the environment and hence the rate controlling effect on the steady state release of the compound to the uterus may be primarily determined by the structure of the deposit itself and the environment in which it is placed. This is extremely beneficial from a manufacturing perspective since once the frame is defined, existing drug formulations or controlled release capsules/fibers may be inserted into the frame. As release rates are primarily determined by the deposits themselves, release rates within the frame should be relatively easily predictable.

The invention may thus also be considered to provide an intrauterine system comprising a frame for receipt of a deposit of a biologically active compound, wherein the frame is an open structure facilitating release of the compound to the uterus. In the following, reference to an open structure allowing access to a substantial part of an outer surface of the deposit is understood to cover an arrangement in which at least 50% of the outer surface of the deposit is exposed. Preferably, more than 60% of the outer surface will be exposed and more preferably more than 70% will be exposed.

The invention further relates to an intrauterine system for the retention of a biologically active compound within the uterus of a female mammal, comprising a deposit of the compound in the form of a generally rod shaped element, a substantially flexible frame defining an interior space for receipt of the deposit and retention elements provided on the frame for retaining the frame within the uterus, wherein the flexible frame and the rod shaped element interact to form a composite structure having greater mechanical strength, in particular stiffness, than either the frame or the rod shaped element alone. Accordingly, an improved structure may be achieved that ensures adequate strength while still ensuring ease of insertion due to the small cross-section of the frame that may be achieved in this manner.

Preferably, the frame stem may have a diameter of less than 4.5 mm, yet more preferably less than 4.0 mm, and may even be less than 3.5 mm in diameter. As the skilled person will understand, for use in combination with a tubular inserter, for surrounding the stem, it is of significance that the IUS is able to fit within an inserter having an outer diameter of 5.0 mm. In this manner compliance may be achieved with ISO-7439.2002, which for human recipients requires an insertion tube of not more than 5.0 mm outer diameter.

According to a preferred embodiment of the invention, the frame comprises an opening for allowing introduction of the deposit into the interior space and a closure member for closing the opening. The opening is preferably located at a forward end of the frame. Once inserted into the interior space, the deposit is thus safely retained against accidental removal from the frame. Alternatively, either the frame or the deposit or both may be sufficiently flexible to allow insertion of the deposit into the frame and its subsequent retention.

Preferably, the closure member comprises a plug. The plug may be integrally formed with the frame or may be a separate component. Although use of a plug or cap is preferred, the skilled man will understand that alternative closures may be used. In particular, the frame may be formed of two parts that join together around the deposit to contain it. Both parts may be connected to close the opening using mechanical means such as press fitting, form fitting, screw thread or the like. Alternatively, the parts may be glued, welded or otherwise bonded together. In a preferred embodiment, the plug is substantially impermeable and can cover and protect an end of the deposit as will be described below.

Most preferably, the frame is formed of a substantially inert material. In this context the term "substantially inert material" is intended to refer to a material that is not eroded by exposure to the environment within the uterus and does not itself actively release an agent. Nevertheless, by the nature of intrauterine devices, it is not excluded that the frame can cause release of leukocytes and prostaglandins by the endometrium. In a most preferred embodiment the frame comprises a biologically compatible polymer, in particular polyethylene (PE), ethylene vinyl acetate (EVA) or a combination thereof. Such polymers have been found to exhibit sufficient strength and resilience for such applications. According to a further preferred embodiment, either the frame or the deposit or both may incorporate an indicator such as a radio-opaque material. Barium sulphate is a preferred substance for this purpose.

In a preferred embodiment of the invention, the one or more retention elements are integrally formed with the frame. The retention elements may take any form that ensures the function of retaining the device within the uterus, including but not limited to an arm or arms, coil structures, anchors, hooks, barbs, fibres and the like. Of importance however is that the retention elements also allow insertion and removal of the device into and from the uterus as appropriate. The frame may preferably comprise an elongate stem in which is located the interior space and the retention elements may then be formed as arms, laterally extending from the stem. The interior space may also be formed at least partially within the retention elements or arms as appropriate. Various forms of arm are well known in the art.

The invention is intended for use with any appropriate deposit. An advantage of the present design is that one form of frame may be manufactured and used as a basis for different deposits carrying different compounds according to the desired treatment. A preferred form of deposit comprises a polymer matrix in which the active agent or compound is dissolved or otherwise dispersed. Preferably the matrix is loaded with a progestogen selected from the group consisting of nomegestrol acetate (NOMAc), natural progesterone, levonogestrel, etonogestrel, dydrogesterone, medrogestone, medroxyprogesterone acetate, megestrol acetate, chlormadinone acetate, cyproterone acetate, gestonorone caproate, demegestone, promegestone, nesterone, trimegestone, norethisterone (norethindrone), norethisterone acetate, lynestrenol, ethinodiol acetate, norethinodrel, norgestrel, norgestimate, dienogest, gestodene, drospirenone, and any other suitable steroidal compound with progestogenic activity. Most preferably the matrix is loaded with etonogestrel within the range of 10-70% wt etonogestrel, but more preferably 30-65 wt % and yet most preferably 40-65 wt %. The core matrix may comprise an EVA polymer, preferably an EVA material with >10% vinyl acetate (VA), more preferably >15% VA %.

According to a further preferred embodiment the rate controlling structure comprises a membrane surrounding the matrix. The membrane preferably also comprises EVA, in particular EVA with a VA percentage of lower than 40%, preferably lower than 33% and most preferably lower than 28%. Such a construction is believed to be most advantageous in ensuring a controlled release of the compound at a steady rate over a prolonged period. Since the membrane forms part of the deposit rather than the frame, each may be optimised independently of the other.

According to a further aspect of the invention, the deposit is substantially form stable and is not eroded during use. Due to the fact that the deposit is not eroded, there is little danger that it could exit from the open structure of the frame during prolonged retention in the uterus. In particular, the frame may be provided with large openings. Another attribute of a form stable deposit is that the mechanical integrity of the IUS remains intact due to interaction of the frame and deposit.

According to a still further aspect of the invention, the deposit may be manufactured in the form of a rod shaped element having a circumferential surface and two end surfaces. Preferred dimensions for the rod are 1.5-3.0 mm diameter and 20-45 mm in length for a single rod although under some circumstances diameters as low as 1.0 mm may provide sufficient release. In general, the dimensions may be largely dictated by standards bodies such as according to the abovementioned ISO-7439.2002, which limits the overall length of an IUD to 36 mm. It will also be understood that different dimensions may be applicable e.g. if the deposit were to be located within an arm of an IUD device. Such deposits have been found convenient to manufacture by extrusion processes and may be subsequently cut into desired lengths for use. In particular, a deposit may be formed by a co-extrusion process to form a rod shaped polymer matrix surrounded by a release rate determining membrane. On cutting the extruded rod into lengths, the exposed ends are not covered by the membrane. In this case, it is desirable that the frame covers the two end surfaces to prevent or reduce release of compound from these regions in particular, the initial burst on commencing use. In this case in particular, it is the membrane around the circumferential outer surface of the deposit that is exposed by the open structure of the frame. To maximise the dosage retained in the deposit and/or to increase the strength of the system, the rod may extend substantially the whole length of the IUD.

The present invention also relates to a method of forming an intrauterine system, the method comprising forming a frame having an interior space and an open structure, providing a deposit of a biologically active compound, the deposit having an outer surface provided with a rate controlling structure and inserting the deposit into the interior space such that a substantial part of the outer surface is exposed through the open structure. In particular, the provision of a deposit of a biologically active compound may involve providing the compound in an existing galenical form for insertion into the frame.

Preferably, the method further comprises applying a closure to an opening in the frame to prevent removal of the deposit from the interior space. The application of the closure may comprise bonding the closure to the frame to prevent removal thereof and may take place in an automated procedure e.g. by gluing, welding or hot stamping. As indicated above, in a preferred embodiment, the opening and its closure is located at a forward end of the frame.

In a further preferred embodiment the method comprises forming the deposit by co-extrusion of a polymer matrix containing the compound and a rate controlling membrane.

According to yet another aspect of the invention the method may comprise forming the frame by injection moulding. The frame and its closure may be formed in a single moulding operation or alternatively may be formed as two distinct components e.g. using different materials.

BRIEF DESCRIPTION OF THE DRAWINGS

The features and advantages of the invention will be further appreciated upon reference to the following drawings, in which.

DESCRIPTION OF ILLUSTRATIVE EMBODIMENTS

Figure 1:
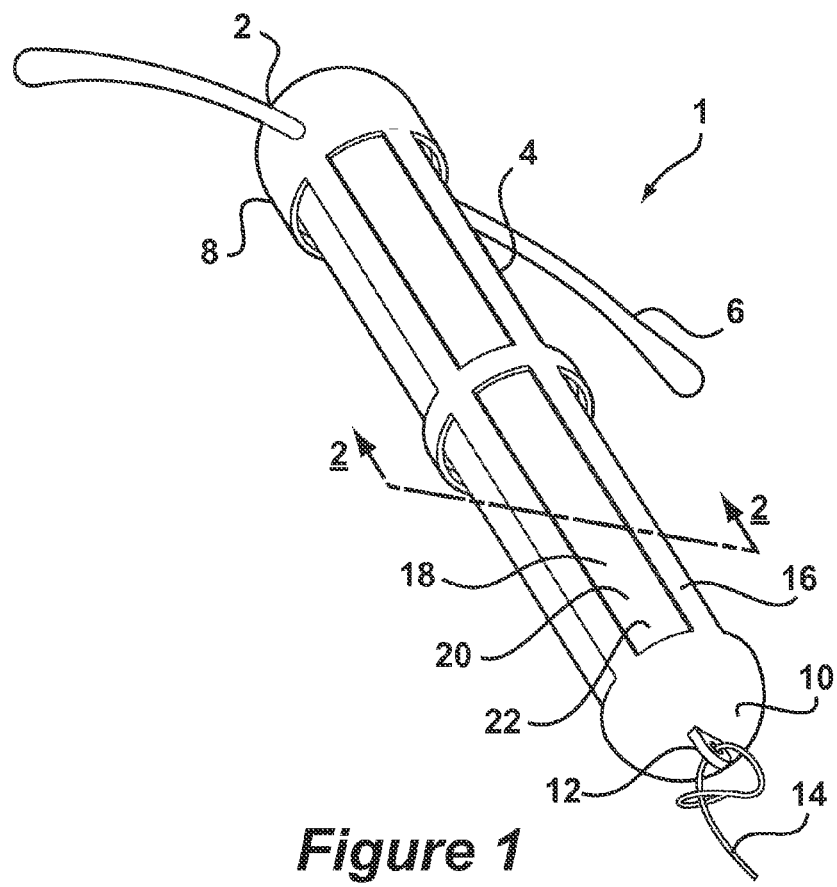
FIG. 1 is a perspective view of a first embodiment of the invention.

Referring to FIG. 1, there is shown an intrauterine system 1 according to a first embodiment of the invention. The IUD 1 has a body 2 comprising a stem 4 with a pair of laterally extending arms 6 connected at its upper end 8. At a lower end 10 of the stem 4, there is provided an eye 12 to which is connected a nylon thread 14. The stem 4 is formed by a frame 16 having openings 18 to an interior space 20. Within the interior space 20 is located a rod shaped deposit 22.

Figure 2:
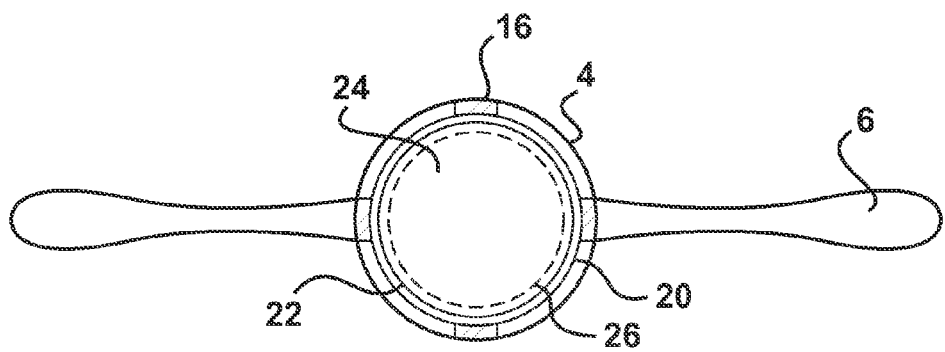
FIG. 2 is a sectional view of the IUD of FIG. 1 along line 2-2.

FIG. 2 shows a cross-sectional view through the IUD 1 taken along line 2-2. FIG. 2 shows more clearly the frame 16 of the stem 4 and the deposit 22 received within the interior space 20. FIG. 2 also shows the deposit 22 to comprise a core 24 and an outer membrane 26. Core 24 is formed of a matrix consisting of EVA copolymer with a vinyl acetate percentage of 28%, to which a quantity of biologically active compound has been added. In the present embodiment, the core 24 is loaded with etonogestrel at 54 wt % with respect to other core materials. The skilled person will be aware that other medications or biologically active compounds may be incorporated and that other loadings may be considered. Additionally, the core 24 comprises 12 wt % of $BaSO_4$ as a radio opaque indicator. The membrane 26 has a thickness of around 40 microns and consists of EVA copolymer with a vinyl acetate percentage of 15%. The skilled person will be aware that other membrane dimensions and compositions may be used, as determined by the desired release rate of the active compound from the core 24. The deposit 22 has an overall length of 30 mm and a diameter of around 2.3 mm. The stem 4 has an overall length of about 36 mm and external diameter of about 3.2 mm.

Manufacture of the IUD 1 takes place by injection moulding of the body 2 in a single piece including stem 4 and arms 6. To this end, the body 2 comprises a PE/EVA mixture including barium sulphate in a 44/36/20 wt % mixture. The presence of barium sulphate improves x-ray visibility of the finished product. The thread 14 is then attached to eye 12 by a simple hitch. After forming the body 2, the rod shaped deposit 22 is inserted into the frame 16 by passing it through one of the openings 18 and sliding it towards the upper end 8. The deposit 22 is sufficiently flexible to allow it to bend slightly into an S-shape such that the other end of the deposit 22 can be inserted into the lower end 10 of the stem 4. The frame 16 is also flexible and assists insertion of the deposit 22. The deposit 22 is now effectively retained within the frame 16 and cannot exit without being manipulated by a user. The IUD is then ready for use and can be conventionally inserted into the uterus of a user by a medical practitioner using an otherwise conventional inserter.

Figure 3:
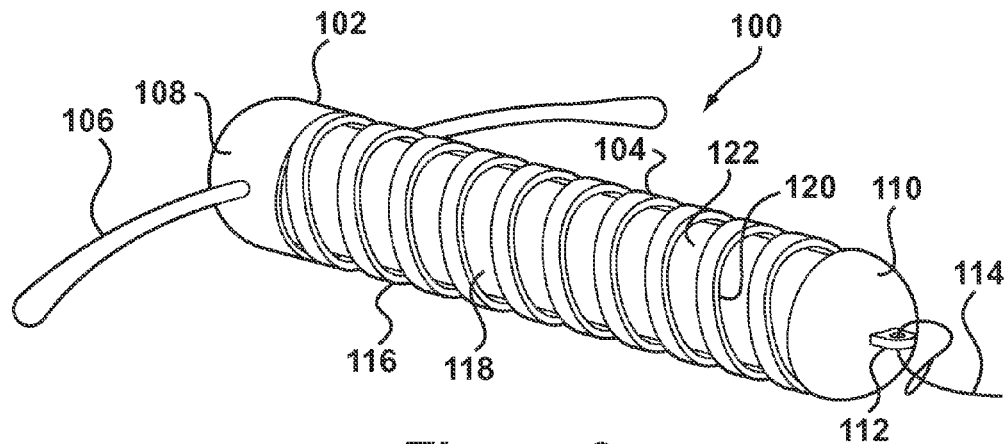
FIG. 3 is a perspective view of a second embodiment of the invention.

FIG. 3 depicts a second embodiment of an IUD 100 according to the invention in which like reference numerals preceded by a 1 will be used to represent the same features as in the system of FIGS. 1 and 2. According to FIG. 3, IUD 100 comprises a body 102 having a stem 104. The stem 104 is formed by a helical coil 116 having openings 118 and an interior space 120. The coil 116 is preferably made of metal but could also be a moulded plastic component. Arms 106 are integrally formed with an upper end 108 of the stem 104 in which the coil 116 is embedded by a moulding procedure. A lower end 110 of the stem 104 is also formed as a moulding and provided with an eye 112 to which is connected thread 114. A deposit 122 is retained in the interior space 120. The deposit 122 may be generally identical to that of FIGS. 1 and 2. Insertion of the deposit 122 into interior space 120 takes place by deformation of the coil 116. Although the thread 114 is depicted as attaching to the lower end 110, it may also be desirable to pass it through the stem 104 to attach at the upper end 108. In this manner, tension on the thread 114 to extract the IUD 100 will not cause stretching of the coil 116.

Figure 4:
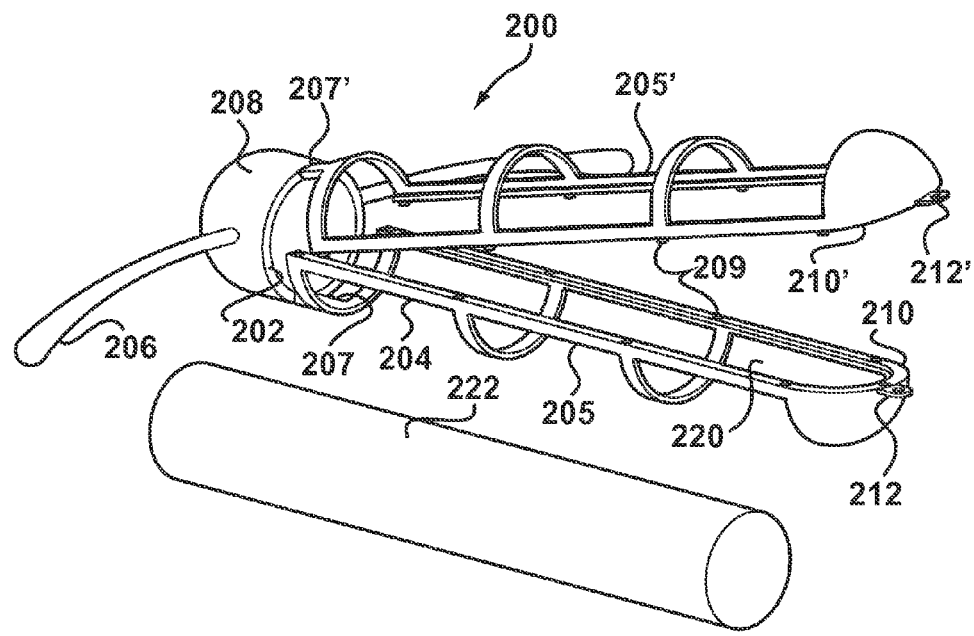
FIG. 4 is a perspective view of a third embodiment of the invention prior to assembly.
Figure 5:
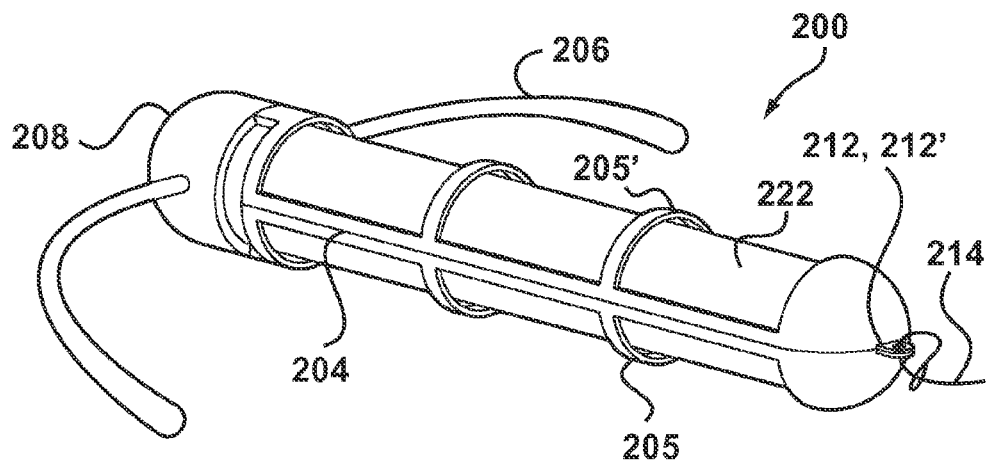
FIG. 5 is a perspective view of the embodiment of FIG. 4 after insertion of a deposit.

FIGS. 4 and 5 depict a third embodiment of an IUD 200 according to the invention in which like reference numerals preceded by a 2 will be used to represent the same features as in the system of FIGS. 1 and 2. According to FIG. 4, the IUD 200 comprises a body 202 having a stem 204 formed in two frame halves 205, 205' having snap elements 209. Eyes 212, 212' are formed at lower ends 210, 210' of frame halves 205, 205'. An upper end 208 of the stem 204 carries a pair of arms 206.

The body 202 is formed in an injection moulding procedure having living hinges 207, 207' between the frame halves 205, 205' and the upper end 208. After insertion of a deposit 222, the frame halves 205, 205' are snapped together to form the stem 204 as shown in FIG. 5. The deposit 222 is now retained in interior space 220. Deposit 222 may be generally identical to that of FIGS. 1 and 2. Thread 214 is then passed through eyes 212, 212' further restraining the frame halves 205, 205' from opening.

Figure 6:
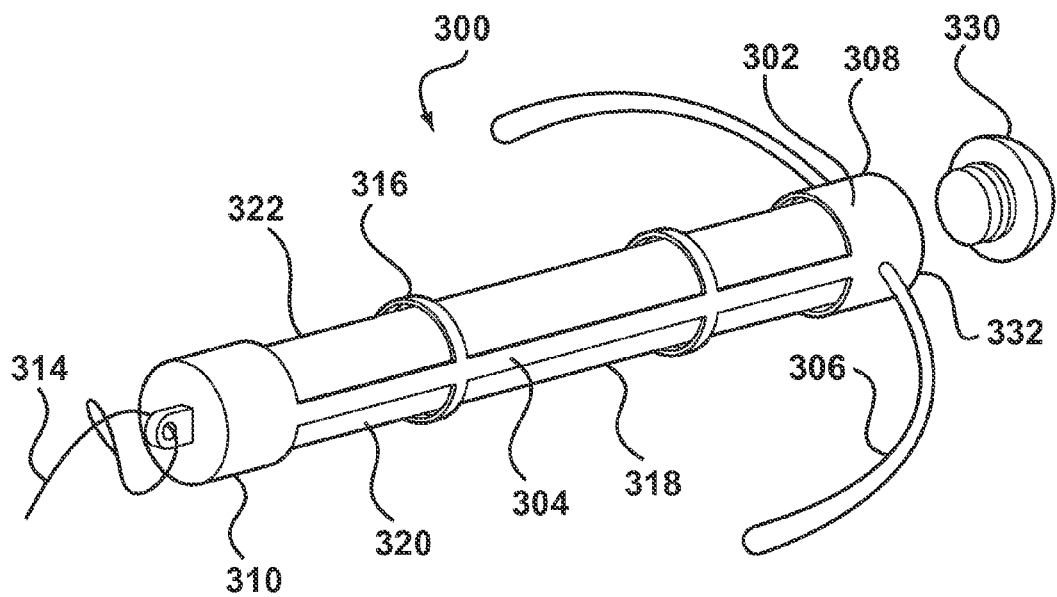
FIG. 6 is a perspective view of a fourth embodiment of the invention.

A fourth embodiment of an IUD 300 according to the invention is disclosed according to FIG. 6 in which like reference numerals preceded by a 3 are used to represent the same features as in the system of FIGS. 1 and 2.

IUD 300 is generally similar to the embodiment of FIG. 1 and comprises a body 302 comprising a stem 304 with a pair of laterally extending arms 306 connected at its upper end 308. At a lower end 310 of the stem 304, there is provided an eye 312 to which is connected a nylon thread 314. The stem 304 is formed as a frame 316 having openings 318 to an interior space 320. Within the interior space 320 is located a rod shaped deposit 322. Unlike the embodiment of FIG. 1, IUD 300 also includes a cap 330 covering an opening 332 formed through the upper end 308. The cap 330 has a smooth outer surface that blends into the upper end 308. The cap 330 allows insertion of the deposit 322 during manufacture of the IUD 300. After insertion the opening 332 is closed by the cap 330 which is fixed in place by a welding procedure. Alternatively or additionally, the cap 330 may be glued to the body 302 using an appropriate adhesive or may be hot stamped thereto, or any other appropriate technique.

Figure 7:
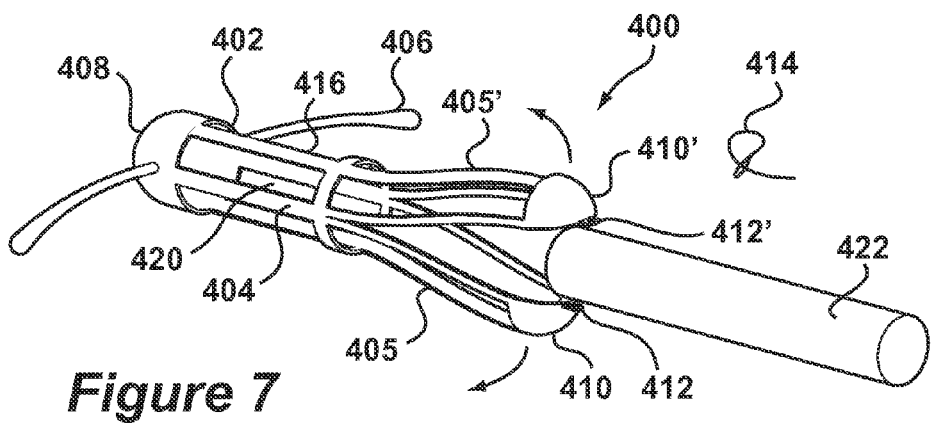
FIG. 7 is a perspective view of a fifth embodiment of the invention during insertion of a deposit.

FIG. 7 depicts a fifth embodiment of an IUD 400 according to the invention in which like reference numerals preceded by a 4 are used to represent the same features as in the system of FIGS. 1 and 2.

Referring to FIG. 7, the IUD 400 has a body 402 comprising a stem 404 with a pair of laterally extending arms 406 connected at its upper end 408. As in previous embodiments, stem 404 is formed as a generally open frame 416. A lower part of the stem 404 is however formed as two flexible legs 405, 405' having mating lower ends 410, 410'. Eyes 412, 412' are formed in the lower ends 405, 405'.

The body 402 is formed in an injection moulding procedure and the legs 405, 405' are sufficiently flexible that they can be spread apart for insertion of a deposit 422. After insertion, the legs 405, 405' return to their original positions. A thread 414 is then passed through eyes 412, 412' to restrain the legs 405, 405' from opening so that the deposit 422 is retained in interior space 420. Legs 405, 405' may also be provided with snap connectors (not shown) at their lower ends 410, 410'.

Figure 8:
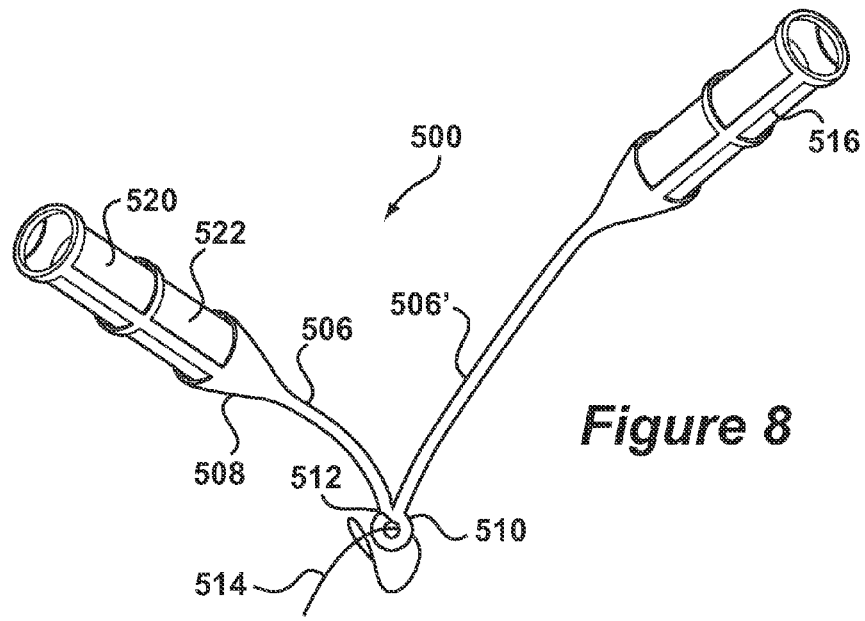
FIG. 8 is a perspective view of a sixth embodiment of the invention.

FIG. 8 depicts a sixth embodiment of an IUD 500 according to the invention in which like reference numerals preceded by a 5 are used to represent the same features as in the system of FIGS. 1 and 2.

Referring to FIG. 8, the IUD 500 comprises a pair of flexible arms 506, 506 joined together connected at their lower ends 510. Each arm 506', 506 carries at its upper end 508 an open frame 516, integrally formed therewith. An eye 512 is formed at lower end 505 to receive a thread 514. As can be seen, one arm 506 is longer than the other 506' and both are sufficiently flexible that they can be folded together for insertion of the IUD into an insertion tube, whereby the frames 516 substantially align with one another within the tube. Each frame 516 comprises an interior space 520 in which a deposit 522 is retained as in previous embodiments.

Figure 9:
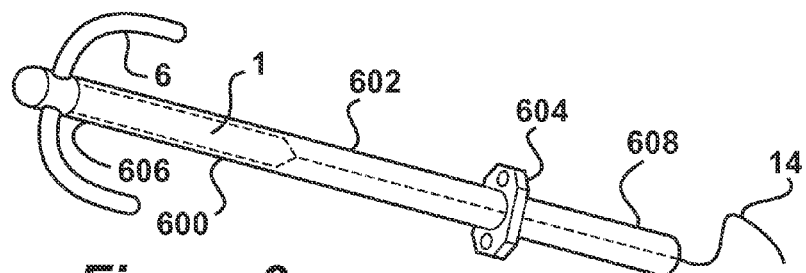
FIG. 9 is a perspective view of an inserter and IUD assembly according to the present invention.

FIG. 9 shows an inserter 600 for introduction of any of the IUDs 1, 100, 200, 300, 400 and 500. The inserter 600 comprises a thin-walled hollow tube 602 having an outer diameter of 3.9 mm and an inner diameter of approximately 3.3 mm. A slideable ruler element 604 is mounted on the tube 602 to assist a medical practitioner in correct positioning of the device. IUD 1 is initially in a refracted position within the inserter with only the arms 6 exposed at a first end 606 of the inserter 600. The thread 14 extends from a second end 608 of the inserter 600, where it can be held by the practitioner. Insertion of the IUD takes place in an otherwise conventional manner and will not be further described here in detail. The IUDs of the present invention may also be used with other inserter arrangements in which the IUD is provided at the end of a wand or holder, rather than within a tubular element. Furthermore, although the arms 6 of the IUD are shown folded around an outside of the inserter tube in the embodiment of FIG. 9, it will be understood that they may also be folded together within the inserter instead.

The invention has thus been described by reference to certain embodiments discussed above. It will be recognized that these embodiments are susceptible to various modifications and alternative forms well known to those of skill in the art without departing from the spirit and scope of the invention. In particular, although all embodiments have been shown with laterally extending, curved arms, other shapes are possible including but not limited to straight, branched and curled arms. Other forms of retention elements may alternatively or additionally be used to maintain the system within the uterus. Accordingly, although specific embodiments have been described, these are examples only and are not limiting upon the scope of the invention.

What is claimed is:

1. An intrauterine system for retention of a biologically active compound within the uterus of a female mammal, the system comprising:

a deposit of comprising a core and an outer membrane, wherein the core comprises a compound, and wherein the membrane controls a rate of release of the compound within the uterus and wherein the core and the membrane substantially form-stable and not eroded during use;

a frame defining an interior space for receipt of the deposit, the frame having an open structure that extends longitudinally along the frame and allows access to a substantial part of an outer membrane of the deposit; and one or more retention elements for retaining the frame within the uterus.

2. The system according to claim 1, wherein the frame is flexible and interacts with the deposit to form a mechanical structure having a stiffness greater than that of either the deposit or the frame alone.

3. The system according to claim 1, wherein the deposit is in the form of a rod shaped element having a circumferential surface and two end surfaces.

4. The system according to claim 1, wherein the frame comprises an opening for allowing introduction of the deposit into the interior space and a closure member for closing the opening.

5. The system according to claim 4, wherein the closure member comprises a substantially impermeable plug.

6. The system according to claim 4, wherein the closure member is located at a forward end of the frame and a retrieval element is located at a rearward end of the frame.

7. The system according to claim 1, wherein the frame is formed of a substantially inert material.

8. The system according to claim 7, wherein the substantially inert material is a biologically compatible polymer.

9. The system according to claim 1, wherein the retention elements are integrally formed with the frame.

10. The system according to claim 1, wherein the deposit comprises a polymer matrix core.

11. The system according to claim 10, wherein the polymer matrix core comprises an EVA polymer comprising more than 10% vinyl acetate and the deposit has a diameter of from 1.0 mm to 3.0 mm.

12. The system according to claim 1, wherein the deposit comprises a rate controlling structure comprising a membrane surrounding the deposit, wherein the membrane comprises an EVA polymer having less than 40% vinyl acetate.

13. The system according to claim 1, wherein the deposit comprises a progestogenic steroidal compound selected from the group consisting of nomegestrol acetate (NOMAc), natural progesterone, levonogestrel, etonogestrel, dydrogesterone, medrogestone, medroxyprogesterone acetate, megestrol acetate, chlormadinone acetate, cyproterone acetate, gestonorone caproate, demegestone, promegestone, nesterone, trimegestone, norethisterone (norethindrone), norethisterone acetate, lynestrenol, ethinodiol acetate, norethinodrel, norgestrel, norgestimate, gestodene, dienogest and drospirenone.

14. The system according to claim 1, wherein the frame having an open structure allows access to at least 50% of a surface of the deposit.

15. The system according to claim 1, wherein the deposit comprises two end surfaces and the frame covers the two end surfaces to prevent release of compound therefrom.

16. The system according to claim 1, wherein the frame comprises an elongate stem in which is located the interior space and the retention elements comprise arms, laterally extending from the stem.

17. The system according to claim 1, further comprising an inserter comprising a hollow tube into which the frame may be received.

18. The system according to claim 17, wherein the inserter has an outer diameter of less than 4.0 mm.

19. A method of contraception in a female mammal, the method comprising placing the intrauterine system according to claim 1 into the uterus of the mammal.

20. An intrauterine system for retention of a biologically active compound within the uterus of a female mammal, the system comprising:

a generally rod shaped deposit of comprising a core and an outer membrane, wherein the core comprises a compound, and wherein the core and the membrane substantially form-stable and not eroded during use;

a substantially flexible frame defining an interior space and having an open structure that extends longitudinally along the frame for receipt of the deposit, wherein the flexible frame and the rod shaped deposit interact to form a composite structure having greater stiffness than either the rod shaped deposit or the frame alone; and one or more retention elements provided on the frame for retaining the frame within the uterus.

21. A method of forming an intrauterine system comprising:

forming a frame having an interior space and an open structure that extends longitudinally along the frame;

providing a deposit comprising a core and a rate controlling outer member, wherein the core comprises a biologically active compound and wherein the core and the membrane substantially form-stable and not eroded during use; and inserting the deposit into the interior space such that a substantial part of the outer membrane is exposed through the open structure.

22. The method according to claim 21, further comprising closing an opening in the frame to prevent removal of the deposit from the interior space.

23. The method according to claim 21, further comprising bonding a closure to the frame to prevent removal of the deposit.

24. The method according to claim 21, wherein the frame is formed by injection moulding.

25. The method according to claim 21, further comprising forming the deposit by co-extrusion of a polymer matrix core containing the compound and a rate controlling membrane.

* * * * *